United States Patent [19]

Polishuk, deceased

[11] 4,151,833

[45] May 1, 1979

[54] METHOD AND APPARATUS FOR DETECTING THE ONSET OF OVULATION

[76] Inventor: W. Z. Polishuk, deceased, 13 Bialik Street 3, late of Jerusalem, Israel, by Alexander Laufer, executor

[21] Appl. No.: 788,407

[22] Filed: Apr. 18, 1977

[30] Foreign Application Priority Data
Apr. 20, 1976 [GB] United Kingdom ..... 16020/76
Jun. 4, 1976 [GB] United Kingdom ..... 23241/76

[51] Int. Cl.² ............................................. A61B 10/00
[52] U.S. Cl. ....................................... 128/738; 73/73; 206/569
[58] Field of Search .................. 128/2 W, 2 R, 270; 23/230 B, 253 TP; 73/73; 206/210, 227, 229, 361, 562, 459, 569

[56] References Cited

U.S. PATENT DOCUMENTS

| | | | |
|---|---|---|---|
| 3,759,375 | 9/1973 | Nappi | 206/210 |
| 3,834,389 | 9/1974 | Dulle | 128/285 |
| 3,889,678 | 6/1975 | Chatterjee et al. | 128/285 |
| 3,898,143 | 8/1975 | Assarsson et al. | 128/285 |
| 3,934,575 | 1/1976 | Bucalo | 128/2 W |
| 4,018,225 | 4/1977 | Elmi | 128/285 |
| 4,018,951 | 4/1977 | Gross | 128/270 X |
| 4,061,846 | 12/1977 | Gross et al. | 128/270 |

*Primary Examiner*—Robert W. Michell
*Assistant Examiner*—Frank Jaworski
*Attorney, Agent, or Firm*—Blanchard, Flynn, Thiel, Boutell & Tanis

[57] ABSTRACT

The onset of ovulation in a female is detected by measuring the water content of the cervical mucus. A pellet made of a water-swellable polymer is inserted into the vagina. The increase in the size of the pellet, that occurs owing to contact with the vaginal mucus for a selected period of time, is measured. The size of the pellet sharply increases at or about the onset of ovulation.

13 Claims, 8 Drawing Figures

METHOD AND APPARATUS FOR DETECTING THE ONSET OF OVULATION

The invention relates to a method and apparatus for detecting the onset of ovulation for the purpose of ascertaining when sexual intercourse is most likely to result in conception. This method and apparatus can therefore be used both as a means of promoting and avoiding conception.

Nowadays, contraceptive techniques may be divided into two groups: invasive methods and non-invasive methods.

Whereas invasive methods, such as the oral administration of various hormone-combinations, in the form of contraceptive pills, and intra-uterine devices, have a high degree of efficiency, the use of contraceptive pills inhibits LH (luteinizing hormone) surge and induces a multitude of metabolic, hormonal and other bodily changes during their intake. In addition, the use of contraceptive pills may give rise to long-lasting effects after cessation of their use. Although the relationship between the use of contraceptive pills and genital malignancy has not been definitely established and appears to be unlikely, the sequential type of contraceptive pill may in some cases produce proliferative changes in the uterus. The list of serious complications following the use of contraceptive pills is considerable and includes the following: thromboembolism, hepatomata, and pseudo-tumor cerebri. Intrauterine devices are produced in more than twenty forms and each of these forms, with its different constituents, such as copper impregnated elements and progesterone carrying elements are known to be responsible for heavy blood loss, abdominal pain, infection and discharge. Thus, although both of these invasive methods of contraception are effective to 95-97%, they are not without serious dangers to a woman's wellbeing. On the other hand, the non-invasive methods of contraception in use today, like the use of pre-coital tablets, creams, foams, diaphragms, and condoms and the reliance on "safe periods" as determined by basal body temperature tests, all carry a considerably high rate of failure and require a very high degree of motivation for successful use.

There is therefore an urgent need for a non-invasive method of contraception that can attain a reasonably low rate of failure.

Any method to determine the day of ovulation could be based on detection of one of the three following endocrine events associated with ovulation: the rapid rise of estradiol, the LH surge or the rise in 17-hydroxy progesterone and progesterone. Any endeavor to predict ovulation must involve the direct determination of serum $E_2$ or T.E. in urine of the metabolic effects of the rapid $E_2$ rise. The daily laboratory determination of $E_2$ in blood or estrogens in urine cannot serve as a popular method of family planning.

One of the parameters of follicular maturation and the rise in estrogen production is the quantity and rheological properties of the cervical mucus. The quantity of cervical mucus increases markedly from 60mg/day, on days 8-9 of the menstrual cycle to a peak of 200-700mg/day at ovulation. This is due mainly to the water content of the cervical mucus. One other important characteristic is the change in cervial mucus viscosity which is at its lowest at ovulation.

It is therefore an object of the present invention to provide a method and apparatus that will give a rapid reading of water content in the vaginal cavity. According to the invention, there is provided a plurality of identical pellets of hydrophilic material which swell on the uptake of aqueous liquid and a gauge comprising an apertured plate.

In use of the method and apparatus according to the invention, during the woman's menstrual cycle, or at least the portion thereof which extends from several days before up to about or after the onset of ovulation, a pellet of hydrophilic material is placed inside the vaginal cavity for a fixed time period during each twenty hours four hours. Conveniently, this is done by inserting the pellet into the vaginal cavity each night and leaving it there for a period of eight hours. It is possible that longer or shorter time periods can be used with satisfactory results, provided that the time period is sufficiently long to cause the size of the pellet to swell to a value indicative of the water content and volume of the vaginal mucus. At the end of this period, the pellet is removed from the vaginal cavity and measured with the apertured gauge. If the pellet is able to pass through the aperture, this indicates that the water content of the cervical mucus has not risen sufficiently to indicate the onset of ovulation.

The process is repeated each day with a fresh pellet until it is found that the pellet has expanded sufficiently in size, as a result of the increase in the water content of the cervical mucus, that it will not pass through the aperture in the gauge. It may then be predicted that ovulation wil take place within a given number of days.

Thus, it has been found by experimentation that the peak variation in the size of the pellets, as a result of the absorption of water from cervical mucus, is closely related to the LH surge and the variation in basal body temperature.

The hydrophilic material of the pellets must be capable of swelling markedly as a result of the variation in the water content of cervical mucus which takes place during each menstrual cycle and must also be a material which is compatible with human tissue.

Copolymers of N-vinyl pyrrolidone and methyl methacrylate, made with or without small amounts (up to 2%) of cross-linking agents, which polymers may have weight percentage water uptakes of up to 100%, or even higher, have been found to be especially suitable for this application. These polymers are in an anhydrous (nonswollen) or substantially anhydrous condition when inserted into the vaginal cavity and they swell as a consequence of contact with the vaginal mucus and uptake of water therefrom. The polymers may be made by a known process of polymerization initiated by a chemical initiator, for example, a peroxide (as in British patent specification No. 1 391,438 and U.S. Ser. No. 530,570, now U.S. Pat. No. 4,032,599, the entire contents of which are incorporated herein by reference, for their description of the compositions and polymerization processes for preparing the hydrophilic polymer). However, polymers made by polymerization initiated by ultraviolet or gamma ray irradiation, as described in British patent specification No. 1,439,132 and U.S. Pat. No. 3,943,043, are of special significance. Polymers produced by the irradiation process are free from the impurities present as a result of the use of initiation additives, and are thus less liable to promote allergic reaction when in contact with human tissue.

In general the invention contemplates the use of physiologically harmless, hydrophilic polymers which will swell by absorption of water, when in contact with the cervical mucus, to a degree indicative of the water content of the cervical mucus. The polymer is anhydrous or substantially anhydrous when it is placed in the vaginal cavity so that the increase in size that occurs will reliably indicate the water content and water volume of the cervical mucus.

One such material which is particularly suitable for this purpose is vinyl pyrrolidone/methyl methacrylate copolymer which is sold under the registered trademark Sauflon 85. In this polymer the volume of the anhydrous polymer is about 17.1% of the volume when the polymer is fully swollen in physiological saline solution.

It has been found that cylindrical pellets of this material, having a diameter of 8mm and a length of 8mm swell to a diameter of up to 12.9mm when the water content of the cervical mucus reaches its peak. Thus, if a gauge is provided with an aperture having a diameter of 11mm, it may be assumed that whenever a pellet has swelled until it can no longer be received in the aperture, then ovulation is imminent and the fertile period has begun.

In certain people a more positive sign of the approach of ovulation may be a sudden rise in vaginal water content. This water content may be monitored by measuring daily the size of the swollen pellet, using a gauge such as the one described hereafter with reference to FIGS. 3 and 4; or by setting a pointer (such as the one described hereafter with reference to FIGS. 5 and 6) to a particular day's pellet diameter and thereby highlighting any large increase in the subsequent day's measurement.

With hydrophilic pellets as described, it is possible to attach a short cord to each pellet for ease of removal of the pellet from the vaginal cavity.

Embodiments of the invention are hereinafter described, by way of example only, with reference to the accompanying drawings.

Figure 1:
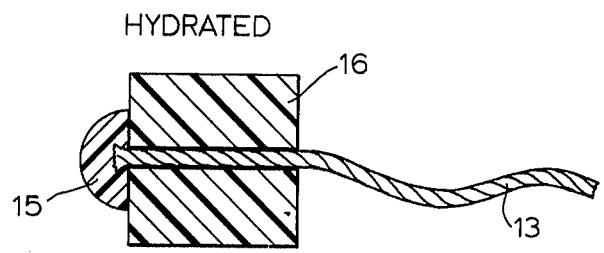
FIG. 1 is a cross-section view through the central axis of a swollen hydrated cylindrical pellet.

The swollen cylindrical pellet 16, shown in FIG. 1, is provided with a cord 13 which is embedded in a cap 15. The cord 13 passes through an aperture along the central axis of the cylindrical pellet and into the cap 15 so as to retain the swollen pellet 16 on the cord 13 and facilitate removal of the swollen pellet 16 from the vaginal cavity by pulling the cord 13.

Figure 2:
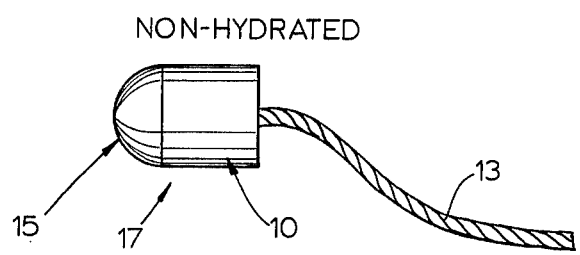
FIG. 2 is an elevation of a non-swollen pellet prior to hydration.

The cylindrical pellet 10, shown in FIG. 2, is in a non-hydrated state. The diameter of the cap 15 and the pellet 10 are substantially equal and the central axes of the cap 15 and the pellet 10 are aligned by the cord 13 so as to facilitate insertion of the assembly 17 into the vaginal cavity. Insertion is further facilitated by the formation of the cap as a dome-shape.

Figure 3:
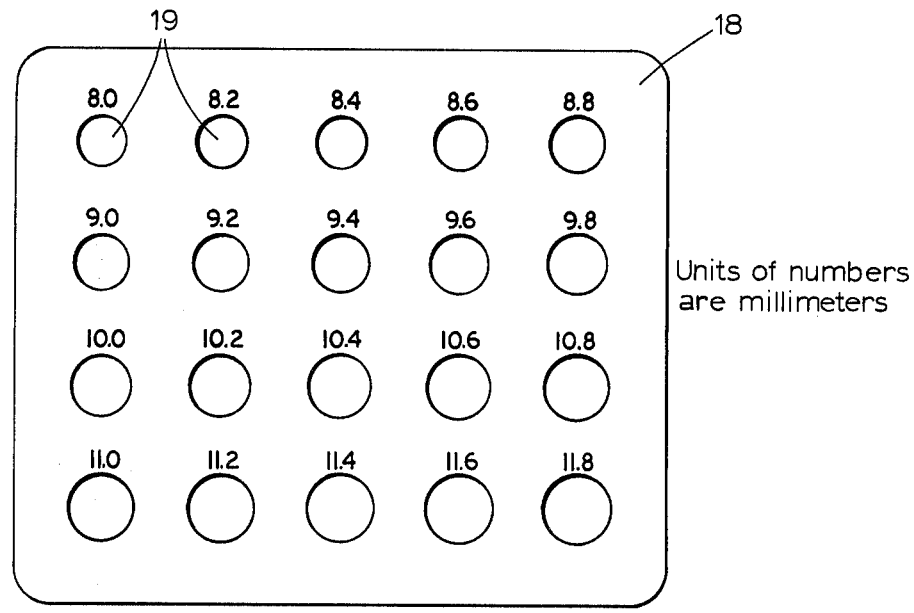
FIG. 3 is a plan view of a gauge provided with a plurality of circular apertures of varying sizes.
Figure 4:
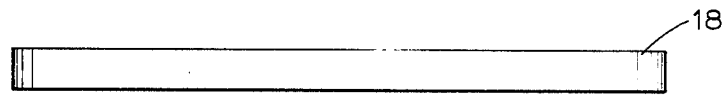
FIG. 4 is an elevation of the gauge in FIG. 3.

The diameter of the swollen cylindrical pellet 16 is measured, in the embodiment shown in FIG. 3, by inserting the swollen pellet into an aperture 19 in the gauge 18, choosing the hole so that a close-fit is achieved and reading the appropriate diameter marked adjacent the aperture. The test of a close-fit in any particular aperture is that the swollen pellet 16 will not fit into the aperture which is next smallest in diameter. The diameter of each of the apertures 19 is indicated by raised numerals formed on the surface of the gauge 18 adjacent their respective apertures. As FIG. 4 shows, the gauge 18 in the embodiment of FIG. 3 is substantially planar. The gauge 18 is conveniently made by injection molding polymethylpentane or polymethylmethacrylate, or a similar transparent plastics material.

Figure 5:
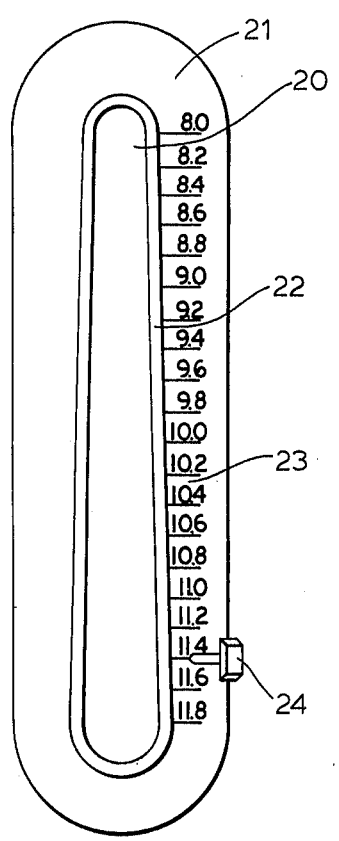
FIG. 5 is a plan view of alternative gauge provided with a graduated tapering aperture and a pointer slideable along the scale.
Figure 6:
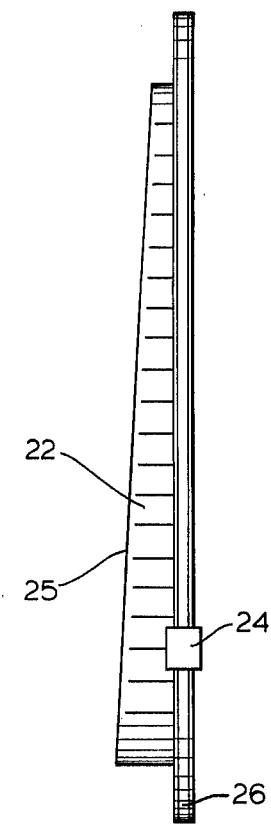
FIG. 6 is a view of the elevation of the gauge in FIG. 5.

FIGS. 5 and 6 are views of an alternative embodiment of a gauge for measuring the size of the swollen pellet 16. The gauge allows measurement of both the diameter and length of the swollen pellet 16 so as to assess more completely the amount of swelling of the pellet 16. The swollen pellet 16 is inserted into the wider end of the tapered aperture 20 in the molding 21 in a direction perpendicular to the plan view in FIG. 5 and is moved towards the narrow end of the tapered aperture 20 until binding between the wall 22 and the swollen pellet 16 prevents further movement in this direction. The width of the tapered aperture 20 at any given point along its length is indicated by graduations and raised numerals on a scale 23 alongside the tapered aperture 20. The number next to the graduation closest to the mean position of the swollen pellet 16 in the tapered aperture 20, indicates the approximate diameter of the swollen pellet 16.

The wall 22 of the tapered aperture 20 also tapers so that its height (measured from the top edge 25 of the wall 22 to the far side of the base plate 26) is equal at all points along its length to the width of the tapered slot at this point. The side of the wall 22 also carries the same gradations as the base plate 26. The swollen cylinder may be moved along the tapered aperture 20 until its length most closely equals the height of the wall 22. The length of the swollen cylinder may then be read from the scale 23.

The pointer 24, which slides along the scale 23, may be set to provide a record of the mean measured length and diameter of the swollen pellet 16 on that day. This may be compared to the next day's measurement and any significantly large increase from day to day may, depending on the particular pattern of vaginal water content changes in any particular person, indicate the onset of ovulation.

Figure 7:
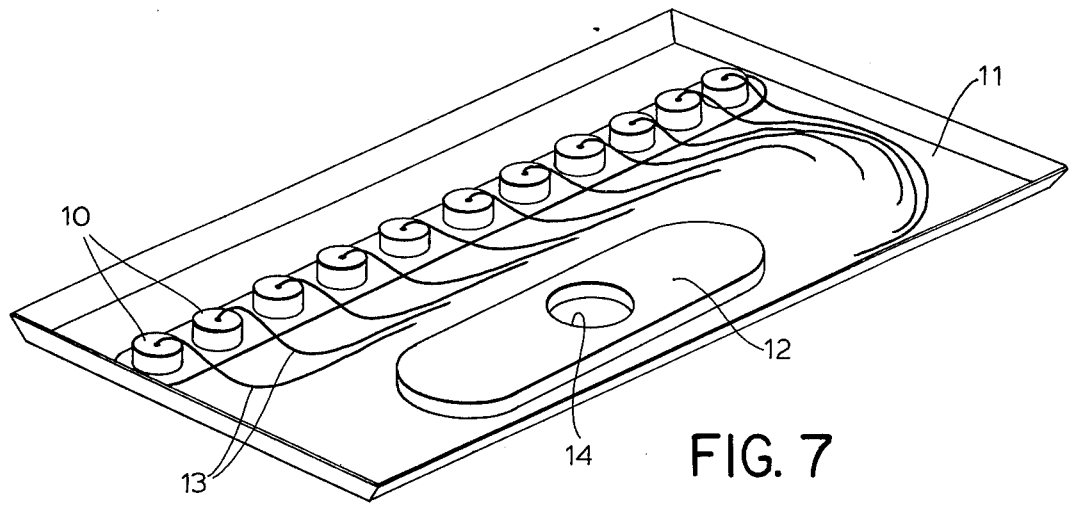
FIG. 7 is a perspective view of a test kit comprising a gauge and a supply of non-hydrated pellets.

In FIG. 7, twelve cylindrical pellets 10 of vinyl pyrrolidone/acrylic copolymer are mounted in a tray 11 which also contains a gauge 12. The pellets 12 are cylindrical in shape having a diameter of 8mm and a length of 8mm. Each pellet 10 is provided with a removal cord 13 which is threaded through a diametral aperture formed in the pellet 10. As shown, the gauge 12 is formed with a circular aperture 14 having a diameter of 11mm.

In use, one of the pellets 10 is placed inside the vaginal cavity each night, for a period of eight hours. Each morning, the pellet 10 is removed, by means of the cord 13, and measured with the gauge 12. If the pellet 10 is small enough to be received within the aperture 14, then it can be said that the fertile period has not yet started and that ovulation is not imminent. When it is found that the swelling of the pellet 10 is such that it cannot be received within the aperture 14 of the gauge 12, it may, in a particular person, indicate that the fertile period has commenced and that ovulation is about to take place.

It has been observed that water content of bovine cervical mucus is maximal at ovulation and similar pattern was found in human cervical mucus, Blair, et al, Nature (Lond) 147:453 (1946); Bommerenke, Am. J. Obst. Gynec. 52:1028 (1946); and Kopito et al, Fertil. and Steril. 24:499 (1973). The utilization of the timing of change in vaginal mucus to a clear slippery discharge, at ovulation, was proposed as a method of family planning, Billings, Lancet 11, 1193 (1972).

EXAMPLE

The correlations between water content of the vaginal mucus, serum LH titers and basal body temperature in 12 women, with regular ovulatory cycles, were studied.

The water content of the vaginal mucus was determined by the degree of expansion due to hydration of cylinders of hydrophilic polymers that were left in the vagina for about 8 hours. These cylinders were made of vinyl pyrrolidone/methyl methacrylate copolymer (Sauflon 85) that were 8mm long with a diameter of 8mm. A perforation in the cylinder allowed threading, for easy handling.

The women were asked to place the hydrophilic cylinders in the vagina at night. The next morning, these cylinders were removed. The degree of hydration was determined by checking the new diameter of the cylinder, in a suitable perforated plate. In all cases, blood for serum LH (RIA) was taken on the morning when the cylinder was removed.

Figure 8:
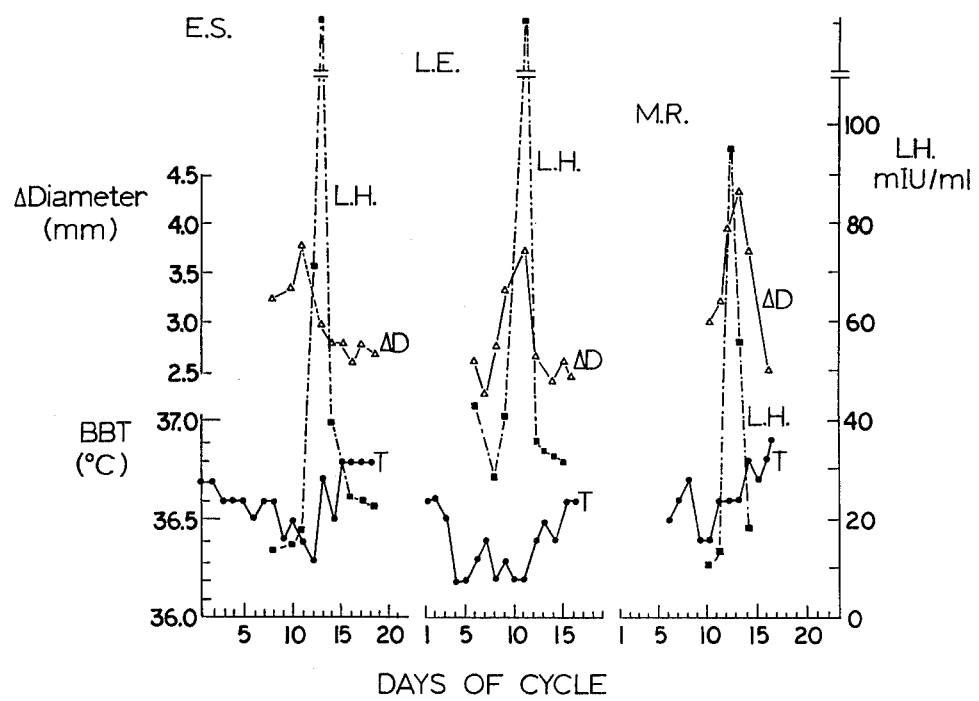
FIG. 8 is a graph showing the relation between size of the pellets, LH readings and basal body temperature, for three typical female humans.

The results showed a close correlation between the serum LH surge and the peak expansion of the cylinder, expressed as "$\Delta$ Diameter" ($\Delta_D$), which is the difference between the initial character of the cylinder and that found after 8 hours in the vagina. The peak in $\Delta_D$ coincided with the LH surge in 6 cases, preceded the LH surge by 24 to 48 hours in 4 cases, and followed the LH surge by 24 hours in 2 cases. There was a similar good correlation with the shift in basal body temperature. The data is shown in FIG. 8.

The maximal $\Delta_D$ reached was 4.6mm. Assuming a $\Delta_D$ limit of 3.2mm, as the beginning of the fertile period, there is defined a relatively short period, between 48 hours before and up to 24 hours after the LH surge. Since the serum LH surge preceeds ovulation by 24h, the $\Delta_D$ may serve as an indication of impending ovulation.

The embodiments of the invention in which an exclusive property or privilege is claimed are defined as follows:

1. A method of detecting the onset of ovulation in a female, which comprises the steps of: once each day, for several days during the menstrual cycle including the days immediately prior to ovulation, inserting into the vagina of said female a pellet made of a physiologically harmless water-swellable, hydrophilic polymer and maintaining said pellet in the vagina for a period of time effective to cause said pellet to swell to a size indicative of the water content and volume of the vaginal mucus; then withdrawing said pellet and measuring the increase of the size of said pellet that occurred while it was present in the vagina, the pellets used the respective days being identical in starting size so that the respective pellets swell to a size indicative of the water content and volume of the cervical mucus for the respective days, whereby the onset of ovulation is indicated when the amount of size increase of one of said pellets exceeds a predetermined minimum size increase or it reaches a peak high value in comparison with the size increase of the pellets used earlier or later in the menstrual cycle.

2. A method according to claim 1 in which the measurement of the size of said pellets is performed by using a plate having aperture means for measuring the size of the pellets.

3. A method according to claim 1 in which said pellets are made of a substantially anhydrous copolymer of N-vinyl pyrrolidone and methyl methacrylate.

4. A kit for use in detecting the onset of ovulation comprising a plurality of identical pellets, each pellet being made of a physiologically harmless, water-swellable, hydrophilic polymer and having a size and shape such that it can be inserted into and removed from the vagina of a female and being capable of being swollen by contact with cervical mucus, and an apertured plate for measuring the sizes of said pellets after they are removed from the vagina.

5. A kit as claimed in claim 4 including means attached to each of said pellets for inserting same into and removing same from the vagina.

6. A kit as claimed in claim 5 in which said means is an elongated flexible element.

7. A kit according to claim 6 in which each of said pellets is cylindrical and said element is a string extending into a central opening in each of said pellets.

8. A kit as claimed in claim 4 in which said plate has a single opening which is larger than the size of said pellets by an amount slightly less than the amount of swelling of the pellets that occurs when said pellets absorb water from the cervical mucus at about the onset of ovulation.

9. A kit as claimed in claim 4 in which said plate has a series of openings of progressively increasing size wherein the smallest opening is smaller than and the largest opening is larger than the size of the pellets when said pellets have been swelled by absorbing water from the cervical mucus at about the onset of ovulation.

10. A kit as claimed in claim 4 in which said plate has an elongated continuously tapered aperture in which said pellets can be slid lengthwise and wherein the minimum width of said aperture is smaller than and the maximum width of said aperture is larger than the width of said pellets when said pellets have been swelled by absorbing water from the cervical mucus at about the onset of ovulation, and a pointer slidably associated with said plate for indicating the size of the last measured pellet.

11. A kit as claimed in claim 10 in which said aperture has a side wall of continuously tapered configuration so that said aperture decreases in depth as it decreases in width.

12. A kit according to claim 4 in which said pellets are made of a copolymer of N-vinyl pyrrolidone and methyl methacrylate.

13. A kit according to claim 4 in which said pellets have a size of about 8mm and the onset of ovulation is indicated when said pellets have been swelled to a size of 11mm or more by contact with the cervical mucus.

* * * * *